(12) United States Patent
Lin

(10) Patent No.: US 6,546,931 B2
(45) Date of Patent: Apr. 15, 2003

(54) SUPRAGLOTTIC AIRWAY STRUCTURE SPECIFICALLY USED FOR ANESTHESIA

(75) Inventor: Bin-Chern Lin, Taichung (TW)

(73) Assignee: Future Top Medical Environment Technic, Co., Ltd., Taipei (TW)

( * ) Notice: Subject to any disclaimer, the term of this patent is extended or adjusted under 35 U.S.C. 154(b) by 0 days.

(21) Appl. No.: 09/734,906

(22) Filed: Dec. 13, 2000

(65) Prior Publication Data

US 2002/0069880 A1 Jun. 13, 2002

(51) Int. Cl.⁷ .............................................. A61M 16/00

(52) U.S. Cl. ............................ 128/207.15; 128/207.14; 128/204.18

(58) Field of Search ....................... 128/200.24, 204.18, 128/207.14, 207.15, 200.26; 604/264; 606/1, 108, 200, 213, 192–210

(56) References Cited

U.S. PATENT DOCUMENTS 5,355,879 A * 10/1994 Brain ................... 128/207.15
RE35,531 E * 6/1997 Callaghan et al. ..... 128/207.15
5,979,445 A * 11/1999 Neame et al. ......... 128/207.15

* cited by examiner

Primary Examiner—Glenn K. Dawson
(74) Attorney, Agent, or Firm—Dennison, Schultz & Dougherty

(57) ABSTRACT

Supraglottic airway (laryngeal mask) structure specifically used for anesthesia, including a silicone mask and a main tube seat with diverging tube opening. The main tube seat is fitted through the silicone mask. The upper and lower faces of the silicone mask are formed with perforations. A rubber annular tube having different diameters is implanted in the silicone mask at the equator thereof. A soft sleeve is fitted on the silicone mask. The inner diameter of the soft sleeve corresponds to the profile of the main tube seat. The soft sleeve has an irregular profile corresponding to the configuration of inner side of the fauces. The soft sleeve is pushed forward to make an upper tube opening of the main tube seat protrude out of the soft sleeve. An anesthetic gas intake tube having an engaging flange is fitted through the diverging section of the main tube seat and engaged therewith. A fine string is used to tie up the soft sleeve, main tube seat and the intake tube so as to prevent the soft sleeve from detaching from the main tube seat. The laryngeal mask is able to completely air-tightly seal the throat of a patient without leakage and over-compressing the mucous membrane of the throat.

9 Claims, 4 Drawing Sheets

SUPRAGLOTTIC AIRWAY STRUCTURE SPECIFICALLY USED FOR ANESTHESIA

BACKGROUND OF THE INVENTION

The present invention is related to a supraglottic airway (laryngeal mask) structure specifically used in anesthesia of a patient who is awake or unconscious. The laryngeal mask has a soft structure with slip-proof and leak-proof effect. In addition, the laryngeal mask is able to completely air-tightly seal the throat of a patient without over-compressing the mucous membrane of the throat.

U.S. Pat. No. 5,355,879 discloses a laryngeal mask construction. One end of an intake tube is fitted with a mask. The bottom of the mask is formed with an opening. An inflating ring is disposed along the periphery of the mask. The inflating ring is connected with an extending inflating tube. The entire mask is placed in the throat (pharynx) of a patient with the tip of the mask leant against the gullet (esophagus) of the patient. The opening of the mask is positioned at the windpipe (larynx) of the patient. Through the inflating tube, the inflating ring is inflated and expanded to eliminate the void between the throat of the patient and the mask. Therefore, the anesthetic gas incoming from the intake tube is prevented from escaping through the void.

The above laryngeal mask enables the anesthetic gas to completely enter human body. However, when 20~30 c.c. air is pumped into the inflating ring the pumping pressure is up to 60~120 cm water column. Such great pressure is exerted onto the mucous membrane of the throat. As a result, it often takes place that mucous membrane of the throat decays after a period of time.

U.S. Pat. No. 5,988,167 discloses a foam cuff for laryngeal mask airway. Such laryngeal mask has an elongated front end adapted to Western body configuration. In addition, such laryngeal mask needs a specific introducer for insertion to avoid the front end of the laryngeal mask reversely folded on the gullet. Insertion of such laryngeal mask needs several experiences to be successful.

SUMMARY OF THE INVENTION

It is therefore a primary object of the present invention to provide a supraglottic airway (laryngeal mask) structure specifically adapted to the inner configuration of the throat. The laryngeal mask has a soft structure which will not over-compress the mucous membrane of the throat.

It is a further object of the present invention to provide the above laryngeal mask structure in which when the anesthetic gas is inspired, the human windpipe and lungs create a reaction force to make the silicone mask inflated so as to seal the windpipe.

It is still a further object of the present invention to provide the above laryngeal mask structure in which a rubber annular tube with different diameters is implanted into the silicone mask to keep the silicone mask in an arch form, whereby the silicone mask can air-tightly attach to the mucous membrane of the fauces.

It is still a further object of the present invention to provide the above laryngeal mask structure which is manufactured at greatly lowered cost.

According to the above objects, the supraglottic airway (laryngeal mask) structure specifically used for anesthesia of the present invention includes a silicone mask and a main tube seat with diverging tube opening. The main tube seat is fitted through the silicone mask. The upper and lower faces of the silicone mask are formed with perforations. A rubber annular tube having different diameters is implanted in the silicone mask at the equator thereof. A soft sleeve is fitted on the silicone mask. The inner diameter of the soft sleeve corresponds to the profile of the main tube seat. The soft sleeve has an irregular profile corresponding to the configuration of inner side of the fauces. The soft sleeve is pushed forward to make an upper tube opening of the main tube seat protrude out of the soft sleeve. An anesthetic gas intake tube having an engaging flange is fitted through the diverging section of the main tube seat and engaged therewith. A fine string is used to tie up the soft sleeve, main tube seat and the intake tube so as to prevent the soft sleeve from detaching from the main tube seat. The laryngeal mask is able to completely air-tightly seal the throat of a patient without leakage and over-compressing the mucous membrane of the throat.

The present invention can be best understood through the following description and accompanying drawings wherein:

DETAILED DESCRIPTION OF THE PREFERRED EMBODIMENT

Figure 1:
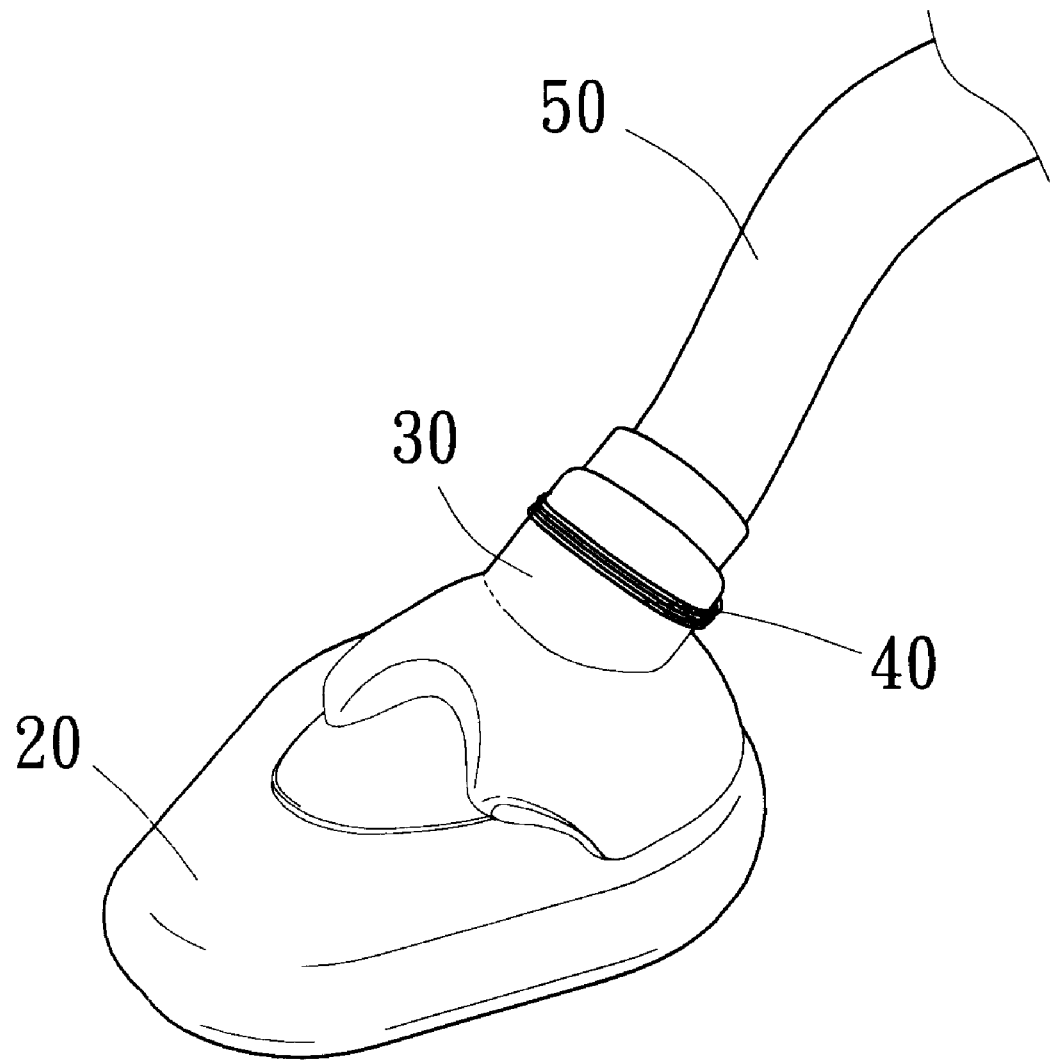
FIG. 1 is a perspective assembled view of the present invention.
Figure 2:
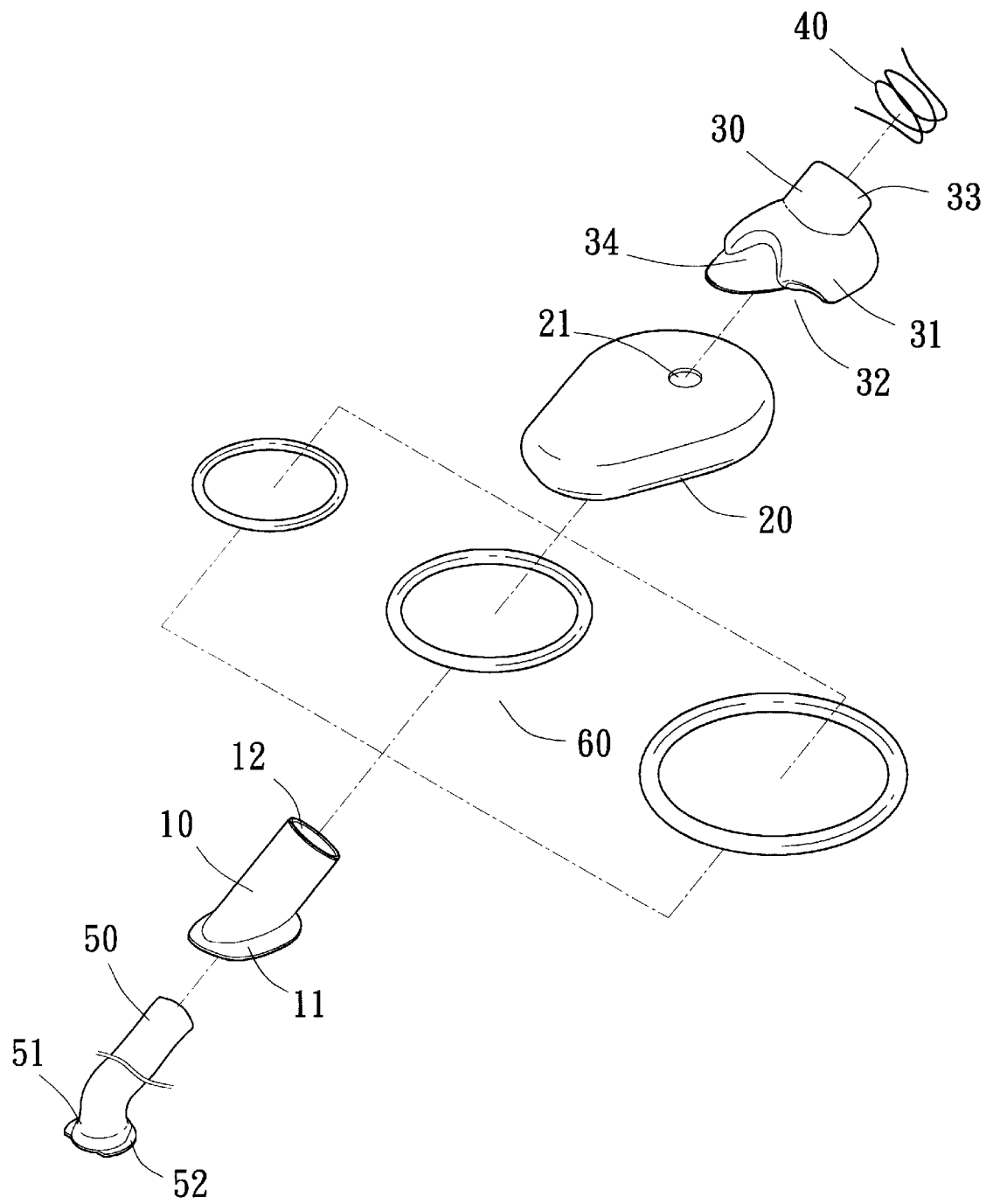
FIG. 2 is a perspective exploded view of the present invention.

Please refer to FIGS. 1 and 2. The present invention includes a main tube seat 10, a silicone mask 20, a soft sleeve 30, a fine string 40, an intake tube 50 and a rubber annular tube 60. The main tube seat 10 is a short tube having an upper and a lower openings 12, 11. The lower tube opening 11 is formed with an oblique cut having a diverging flange.

The silicone mask 20 is a substantially elliptic body. The upper face of the elliptic body is formed with a small perforation 21. The lower face of the elliptic body is formed with a larger arch slot 22. The peripheries of the perforation 21 and the slot 22 have a certain thickness for enhancing the tightness.

The soft sleeve 30 is made of elastic rubber or silicone material and is formed with a profile adapted to the configuration of the main tube seat 10. The upper end of the sleeve 30 is formed with a tube mouth section 33. The lower end of the sleeve 30 is formed with a diverging edge 31 with large area. Two sides of the diverging edge 31 are respectively formed with two notches 32. The diverging edge 31 is further formed with a recessed section 34 between the notches 32.

The fine string 40 is made of a filament and tightly tied around the middle portion of the tube mouth section 33 of the sleeve 30 so as to prevent the sleeve 30 from detaching from the main tube seat 10.

The intake tube 50 is a tube body with a certain length. The lower opening of the intake tube 50 is formed with an inclined section 51. An engaging flange 52 is formed on the inclined section 51 along about ¾ of the rear edge of the inclined section 51.

The rubber annular tube 60 is accommodated in the silicone mask 20 and is formed with different diameters.

Referring to FIG. 1, the upper tube opening 12 of the main tube seat 10 is fitted through the arch slot 22 of the bottom face of the silicone mask 20 into the perforation 21 thereof. The diverging lower tube opening 11 of the main tube seat 10 is engaged with the periphery of the perforation 21. Then the soft sleeve 30 is fitted onto the upper tube opening 12 of the main tube seat 10 and pushed to the bottom thereof. The upper tube opening 12 of the main tube seat protrudes out of the tube mouth section 33 of the soft sleeve 30. Then the intake tube 50 is fitted into the lower tube opening 11 of the main tube seat 10 with the engaging flange 52 of the inclined section 51 of the intake tube 50 engaged with the rear edge of the lower tube opening 11 of the main tube seat 10. The fine string 40 is used to tie up the soft sleeve 30, main tube seat 10 and the intake tube 50 and prevent the soft sleeve 30 from detaching from the main tube seat 10. Finally, the rubber annular tube 60 with different diameters is implanted into the silicone mask 20 to keep the silicone mask 20 in an arch form, whereby the silicone mask 20 can air-tightly attach to the mucous membrane of the fauces.

Figure 3:
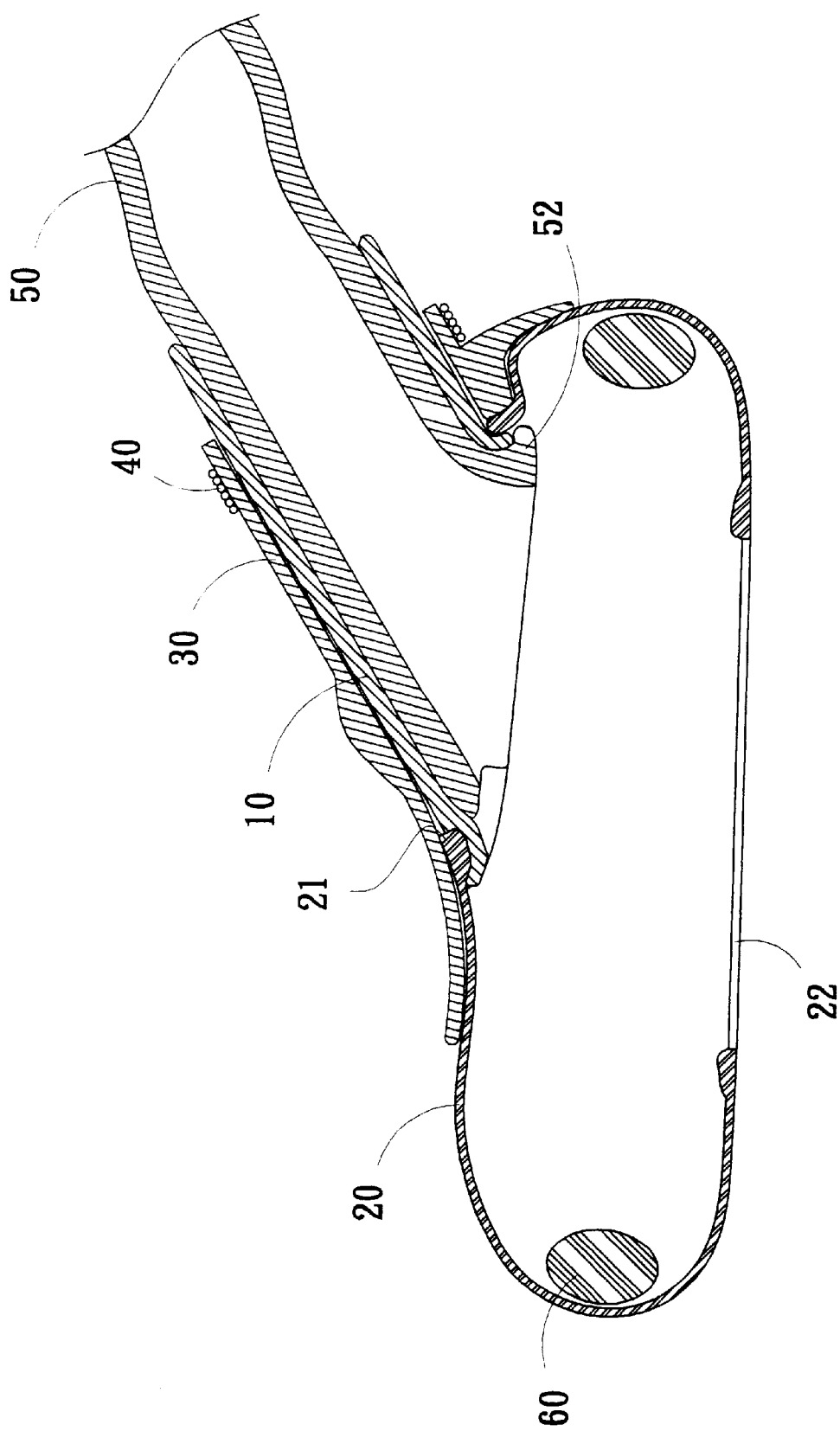
FIG. 3 is a sectional assembled view of the present invention.
Figure 4:
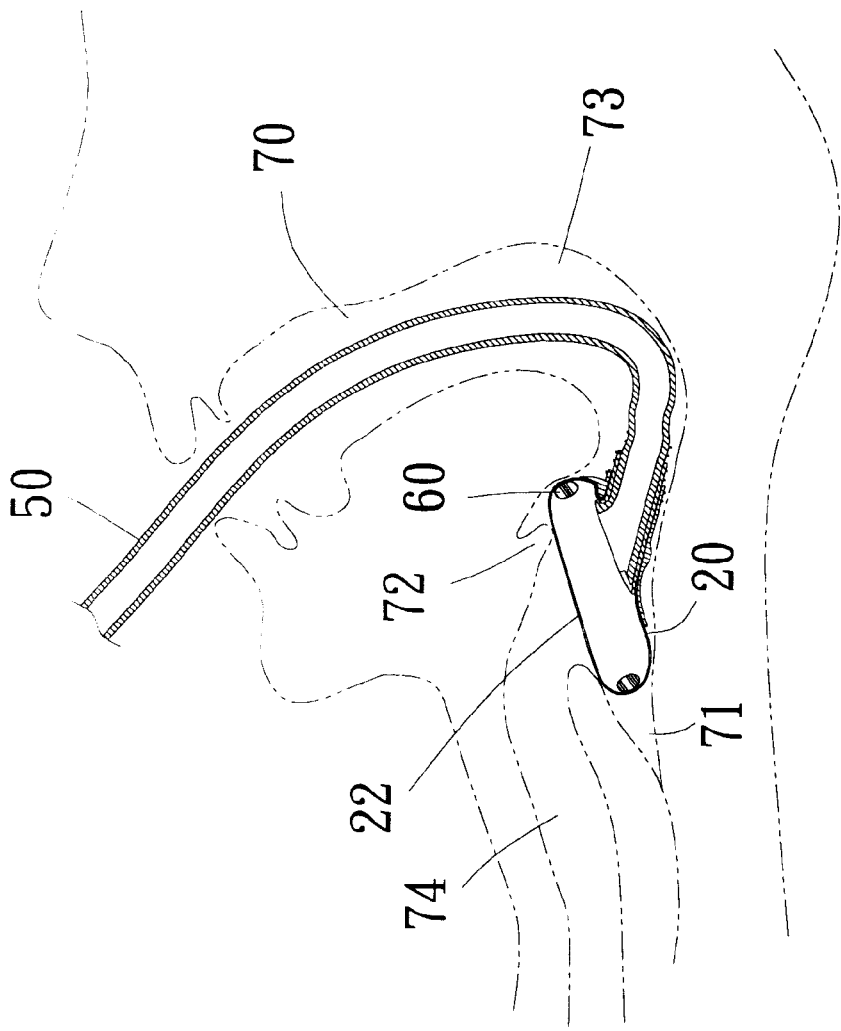
FIG. 4 is a sectional view showing the use of the present invention.

Referring to FIGS. 3 and 4, when applied to human body, the mask body formed by the silicone mask 20 and the soft sleeve 30 enclosing the rubber annular tube 60 is placed into the oral cavity 70 of a patient with the arch slot 22 facing downward. Then the mask body is further pushed forward along the arch of the throat 73 to make the arch slot 22 of the bottom face of the mask body right positioned above the windpipe 74. Through the intake tube 50, the anesthetic gas is conducted into the windpipe 74. According to the action/reaction force principle, the windpipe and the lungs will create a reaction force (the pressure of the gas entering from the intake tube 50) to make the silicone mask 20 with the rubber annular tube 60 automatically inflated again to air-tightly attach to the mucous membrane of the fauces and completely seal the throat 73 without leaving any void. Therefore, the anesthetic gas will not escape and can be precisely controlled in amount.

When the anesthetic gas is inspired, the human windpipe and lungs create a reaction force to make the silicone mask automatically inflated so as to achieve an airtight effect. The supraglottic airway (laryngeal mask) of the present invention is used without any other auxiliary implement. Moreover, the laryngeal mask of the present invention is able to completely air-tightly seal the throat of the patient without over-compressing the mucous membrane of the throat. Therefore, the anesthetic gas will not escape and the amount thereof can be precisely controlled.

The above embodiment is only used to illustrate the present invention, not intended to limit the scope thereof. Many modifications of the above embodiment can be made without departing from the spirit of the present invention.

What is claimed is:

1. Supraglottic airway structure used for anesthesia, comprising a silicone mask and a main tube seat with diverging tube opening, the main tube seat being fitted through the silicone mask, a rubber annular tube being implanted in the silicone mask, a soft sleeve being fitted on the silicone mask, the soft sleeve being pushed forward to make an upper tube opening of the main tube seat protrude out of the soft sleeve, an anesthetic gas intake tube having an engaging flange being engaged with the main tube seat, a fine string being used to tie up the soft sleeve, main tube seat and the intake tube so as to prevent the soft sleeve from detaching from the main tube seat.

2. Supraglottic airway structure used for anesthesia as claimed in claim 1, wherein the silicone mask is formed with two perforations, the two perforations having thickened peripheries for enhancing tightness.

3. Supraglottic airway structure used for anesthesia as claimed in claim 2, wherein one of said two perforations of the silicone mask has a diameter smaller than that of the upper tube opening of the main tube seat.

4. Supraglottic airway structure used for anesthesia as claimed in claim 2, wherein one of said two perforations of the silicone mask has a diameter not larger than that of the diverging opening of the main tube seat.

5. Supraglottic airway structure used for anesthesia as claimed in claim 1, wherein the engaging flange of the intake tube is formed along about ¾ of the periphery of the intake tube.

6. Supraglottic airway structure used for anesthesia as claimed in claim 1, wherein said silicone mask includes an equator and wherein the rubber annular tube is positioned in the silicone mask at the equator thereof.

7. Supraglottic airway structure used for anesthesia as claimed in claim 6, wherein the silicon mask is adapted to accommodate rubber annular tubes of varying diameters.

8. Supraglottic airway structure used for anesthesia as claimed in claim 1, wherein the soft sleeve has an inner diameter which corresponds to the main tube seat.

9. Supraglottic airway structure used for anesthesia as claimed in claim 8, wherein the soft sleeve has an irregular profile corresponding to the configuration of inner side of the fauces.

* * * * *